United States Patent [19]
Kato et al.

[11] Patent Number: 4,465,938
[45] Date of Patent: Aug. 14, 1984

[54] APPARATUS FOR DETECTING A PARTICLE AGGLUTINATION PATTERN

[75] Inventors: Masahiko Kato, Akigawa; Tokio Kano, Akishima, both of Japan

[73] Assignee: Olympus Optical Co., Ltd., Japan

[21] Appl. No.: 373,100

[22] Filed: Apr. 29, 1982

[30] Foreign Application Priority Data

May 7, 1981 [JP] Japan .................................. 56-67583

[51] Int. Cl.$^3$ ............................................. G01N 15/06
[52] U.S. Cl. ..................................... 250/576; 356/246
[58] Field of Search ....................... 356/244, 246, 440; 250/573, 574, 575, 576

[56] References Cited

U.S. PATENT DOCUMENTS 3,883,308  5/1975  Matte .................................. 356/246
4,226,531  10/1980  Tiffany et al. ....................... 250/576

Primary Examiner—David C. Nelms
Attorney, Agent, or Firm—Parkhurst & Oliff

[57] ABSTRACT

An apparatus for detecting photoelectrically a particle agglutination pattern formed on a conical bottom surface of a reaction vessel is disclosed. A lamp and a diffusion plate are arranged above the reaction vessel to illuminate the particle pattern and an objective lens and a light detector are arranged underneath the reaction vessel to form an image of the particle pattern on the light detector. In order to prevent a relatively sharp image of the diffusion plate from being formed on the light detector, an optical correction plate having a conical projection formed in its lower surface is arranged immediately below the reaction vessel. The optical correction plate may be secured to a lower surface of the reaction vessel or may be integrally formed with the reaction vessel on its lower surface.

24 Claims, 11 Drawing Figures

APPARATUS FOR DETECTING A PARTICLE AGGLUTINATION PATTERN

BACKGROUND OF THE INVENTION

The present invention relates to an apparatus for detecting a particle agglutination pattern formed on an inclined bottom surface of a reaction vessel due to immunological agglutination reaction, and more particularly to an apparatus for determining various types of blood, existence of antigens and antibodies by detecting a blood corpuscular agglutination pattern formed on a conical bottom surface of a reaction vessel.

Various kinds of such detecting apparatuses have been proposed. In one of them, use is made of a reaction vessel made of transparent material and having a conical bottom surface. When an agglutination reaction proceeds in the reaction vessel, agglutinated particles are uniformly deposited on the inclined bottom surface just like as snow to form a uniformly deposited pattern. Contrary to this, when no agglutination reaction occurs, descending particles roll down along the inclined bottom surface and are collected at the lowermost central portion of the bottom to form a centrally collected pattern. Therefore, by detecting photoelectrically the particle pattern formed on the bottom surface, it is possible to known whether the agglutination reaction has occurred or not.

However, in the known apparatus, the reaction vessel is made of material having a refractive index different from that of the surrounding air and thus, the bottom wall serves as a kind of concave lens. Therefore, an image of the bottom surface formed on a light detector has not uniform brightness, but has greater brightness at its center than periphery. This results in that the particle agglutination pattern could not be accurately detected and sometimes erroneous judgement might be effected.

SUMMARY OF THE INVENTION

The present invention has for its object to provide an apparatus for detecting photoelectrically a particle agglutination pattern formed on an inclined bottom surface of a reaction vessel, which apparatus can obviate the above mentioned drawbacks of the known apparatus and can detect the particle agglutination pattern in a very accurate and precise manner.

According to the invention an apparatus for detecting photoelectrically a particle agglutination pattern formed on a bottom surface of a reaction vessel, at least a part of the bottom surface being inclined with respect to the horizontal plane, comprises means for illuminating the particle agglutination pattern formed on the bottom surface of the reaction vessel;

means for forming an image of the particle agglutination pattern formed on the bottom surface;

means for converting the image of the particle agglutination pattern into an electrical signal representing the particle agglutination pattern; and means arranged underneath the reaction vessel and having a projection a contour of which is substantially identical with that of the bottom surface to correct a nonuniformity in brightness of an image of the bottom surface of the reaction vessel formed on the converting means.

DESCRIPTION OF THE PREFERRED EMBODIMENTS

Figure 1:
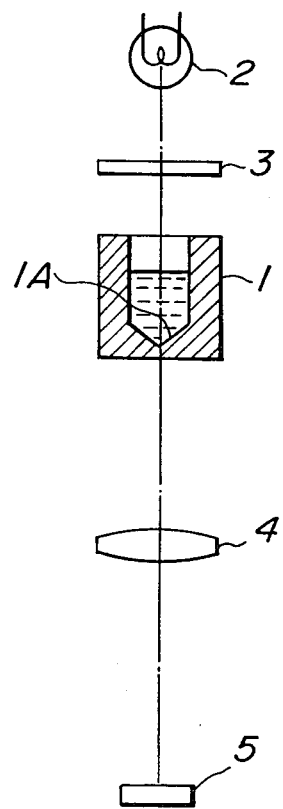
FIG. 1 is a schematic view showing a known apparatus for detecting a particle agglutination pattern.
Figure 2:
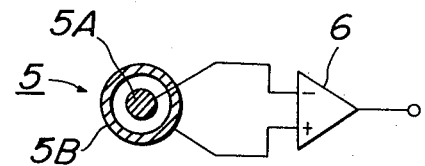
FIG. 2 is schematic view illustrating a construction of a light detector of the apparatus shown in FIG. 1.

FIG. 1 illustrates a construction of an optical system of a known particle agglutination pattern detecting apparatus. A particle pattern formed on a conical bottom surface 1A of a transparent reaction vessel 1 is illuminated by light emitted from a light source 2 such as a tungsten lamp by means of a diffusion plate 3 and an image of the particle pattern is formed by an objective lens 4 onto a light detector 5. As shown in FIG. 2, the light detector 5 comprises a circular light receiving region 5A and a ring-shaped light receiving region 5B arranged concentrically with the region 5A. These regions 5A and 5B are so constructed that when the agglutination reaction occurs and the uniformly deposited particle pattern is formed on the bottom surface 1A, they produce output signals having substantially same amplitudes, but when the centrally collected particle pattern is formed due to absence of the agglutination reaction, the ring-shaped light receiving region 5B produces an output signal having a larger amplitude and the circular light receiving region 5A produces an output signal having a smaller amplitude. Therefore, by deriving a difference between the output signals of the light receiving regions 5A and 5B by means of a differential amplifier 6, it is possible to detect whether or not the agglutination reaction has occurred in the reaction vessel. That is to say, in case that the uniformly deposited particle pattern is formed due to the agglutination reaction, the differential amplifier 6 produces an output signal of very small amplitude, but when the centrally collected particle pattern is formed, the amplifier 6 produces an output signal of a very large amplitude.

Figure 3:
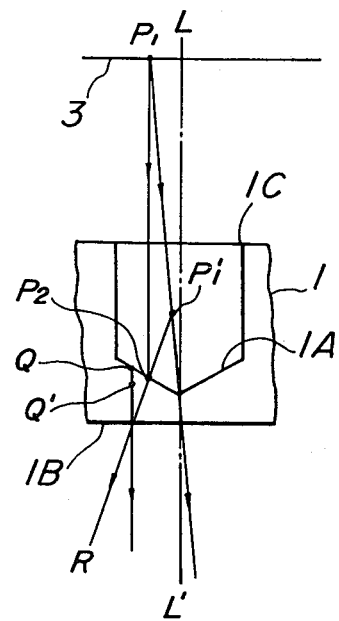
FIGS. 3 and 4 are schematic views for explaining how to produce a non-uniform brightness distribution in an image of the bottom surface in the known detecting apparatus.
Figure 4:
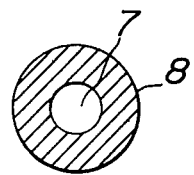

In the known detecting apparatus, when an image of the bottom surface 1A of the reaction vessel 1 is formed on the light detector 5 while the vessel is kept vacant, it is impossible to obtain the bottom image having a uniform brightness distribution, but there is produced a brighter area 7 at a center of the bottom image 8 as schematically illustrated in FIG. 4. This will be theoretically explained as follows. In FIG. 3, a light ray emitted from an arbitrary point $P_1$ on the diffusion plate 3 toward a point $P_2$ on the bottom surface 1A of the reaction vessel 1 is refracted by the bottom surface 1A and is further refracted by a rear surface 1B of the reaction vessel 1 in a direction R. Therefore, this light ray is seemed to emanate from a point $P_1'$ which is much closer to the bottom surface 1A. Contrary to this, a light ray emanating from an arbitrary point Q on the bottom surface 1A is seemed to generate from a point Q' which is lower than the point Q by a distance depending upon a refractive index of the reaction vessel material. In this manner, the bottom wall of the reaction vessel 1 defined by the bottom surface 1A and the rear surface 1B forms a kind of a concave lens which forms an imaginary image of the diffusion plate 3 at a plane which includes the point $P_1'$ and situates quite near measured in an optical axis L—L' to an imaginary image of the bottom surface formed by the concave lens at a plane including the point Q'. Further, in general, the objective lens 4 has a rather long focal depth in order to form a sharp image of the pattern formed on the inclined bottom surface 1A and therefore, the imaginary image of the diffusion plate 3 as well as the imaginary image of the particle pattern are substantially equally focused on the light detector 5. That is to say, a relatively sharp image of the light source is formed on the light detector 5. In this case, a circular boundary of the upper edge 1C of the reaction vessel 1 serves as a kind of stop or diaphragm and thus, there is produced the distinct brighter portion 7 at the center of the bottom image 8. Moreover, the center of the brighter portion 7 could not be always made coincident with the center of the light detector 5. Therefore, the signal produced from the differential amplifier 6 has a relatively small signal to noise ratio and thus, the particle agglutination pattern could not be detected with a high precision.

Further, it has been also known to arrange the light source 2 and diffusion plate 3 below the reaction vessel 1 and arrange the objective lens 4 and light detector 5 above the reaction vessel 1 so as to illuminate the reaction vessel 1 from the underneath thereof. In such an apparatus a light ray emitted from an arbitrary point P of the diffusion plate 3 toward a point Q on an outer bottom surface 1B of the vessel 1 is refracted by the rear surface 1B and the bottom surface 1A and thus is seemed to emanate from a point P' on the diffusion plate 3 which is much closer to an optical axis L—L' than the point P. Therefore, also in this case a central portion of the light detector 5 is illuminated with stronger light although a distinct brighter portion 7 shown in FIG. 4 is not produced.

The present invention is to obviate or at least reduce the drawback of the known apparatuses by arranging an optical correction plate which serves to compensate the refracting action of the concave lens.

Figure 6:
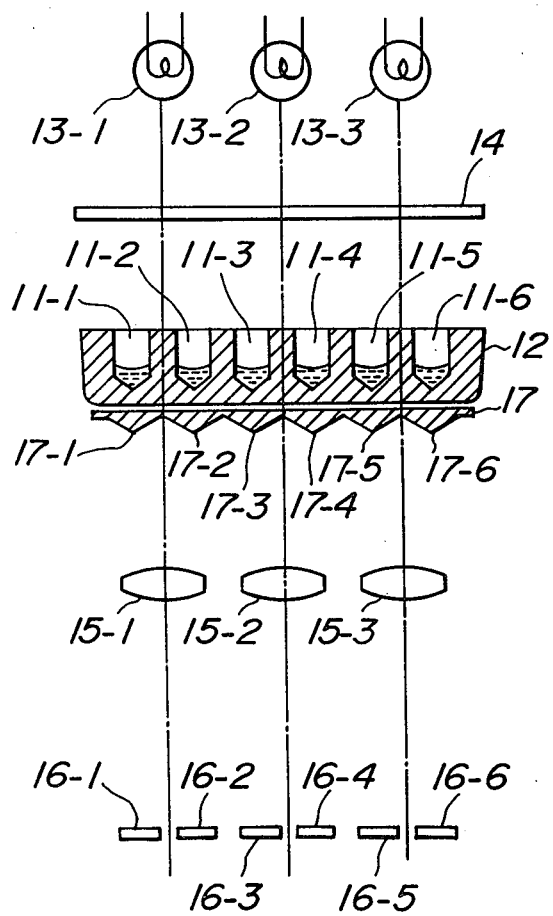
FIG. 6 is a schematic view showing an embodiment of the detecting apparatus according to the invention.
Figure 7:
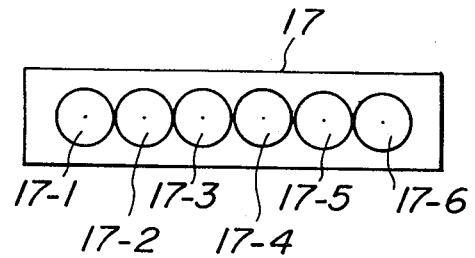
FIG. 7 is a plan view illustrating an optical correction plate shown in FIG. 6.

FIG. 6 is a schematic view showing an embodiment of the particle agglutination pattern detecting apparatus according to the invention. In this embodiment use is made of a microplate 12 in which are formed a number of reaction vessels 11 in a matrix form and particle agglutination patterns formed on conical bottom surfaces of reaction vessels 11-1 to 11-6 in a row are simultaneously detected. The reaction vessels 11-1 to 11-6 are illuminated by light sources 13-1 to 13-3 such as tungsten lamps via a diffusion plate 14 and images of the particle patterns formed on the bottom surfaces of the reaction vessels 11-1 to 11-6 are formed by means of objective lenses 15-1 to 15-3 on light detectors 16-1 to 16-6, respectively. Each light detector comprises a circular light receiving region and a ring-shaped light receiving region arranged coaxially with the circular light receiving region, and the pattern can be identified by deriving a difference between output signals from the two regions just like as shown in FIG. 2. According to the invention underneath the microplate 12 is arranged an optical correction plate 17 having an array of a conical projections 17-1 to 17-6. FIG. 7 is a plan view showing the optical correction plate 17 from that side on which the projections are formed. The correction plate 17 is so arranged with respect to the microplate 12 that an apex of each conical projection is made aligned with the lowermost bottom center of the related reaction vessel. The optical correction plate 17 may be made of various kinds of transparent material and it is preferable to manufacture the plate 17 by the same material as the microplate 12.

By providing the optical correction plate 17 immediately below the microplate 12, it is possible to project a uniform image of the bottom surface of reaction vessel on the light detector. This will be explained in detail hereinbelow.

Figure 8:
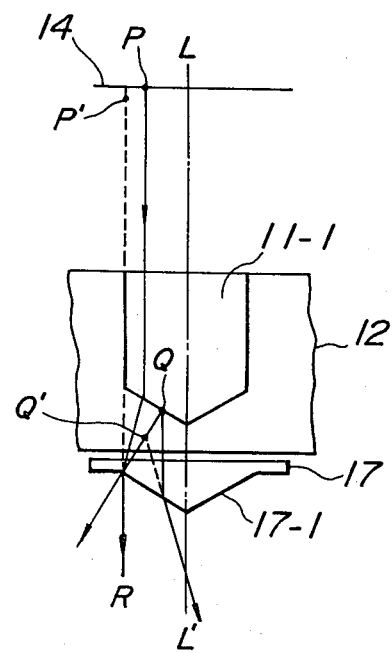
FIG. 8 is a schematic view for explaining how to generate a uniformity in brightness of an image of a bottom surface of a reaction vessel according to the invention.

As shown in FIG. 8, a light ray emitted from an arbitrary point P on the diffusion plate 14 is refracted by the bottom surface of the reaction vessel 11-1, is made incident upon the plate 17, and is further refracted by its projection 17-1 in a direction R. Therefore, this light ray is seemed to emanate from a point P' which is slightly lower than the diffusion plate 14. Whereas, a light ray emanating from an arbitrary point Q on the bottom surface is refracted by the conical projection 17-1 and is seemed to emanate from a point Q'. That is to say, an imaginary image of the diffusion plate 14 is formed near the diffusion plate and an imaginary image of the bottom surface is formed underneath the bottom surface. Therefore, there is a very large spacing viewed in an optical axis L—L' between these imaginary images and thus, even if the objective lens 15-1 has a large focal depth, a sharp image of the diffusion plate 14 is not formed on the light detector 16-1. In this manner, according to the invention the light detectors 16-1 to 16-6 are uniformly illuminated when the reaction vessels 11-1 to 11-6 do not contain test liquid and thus, it is possible to obtain an electric signal having a very high signal to noise ratio and to detect the particle patterns formed on the reaction vessels with a high precision even though the center of the light detectors 16-1 to 16-6 are not made aligned with the centers of the reaction vessels 11-1 to 11-6. It should be noted that in the above explanation possible refraction caused at the opposite surfaces of the microplate 12 and the optical correction plate 17 are neglected.

Figure 5:
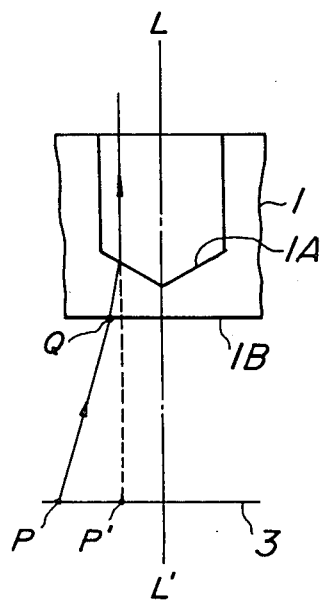
FIG. 5 is a schematic view for explaining how to produce a non-uniformity of brightness in an image of a bottom surface in another known detecting apparatus.
Figure 9:
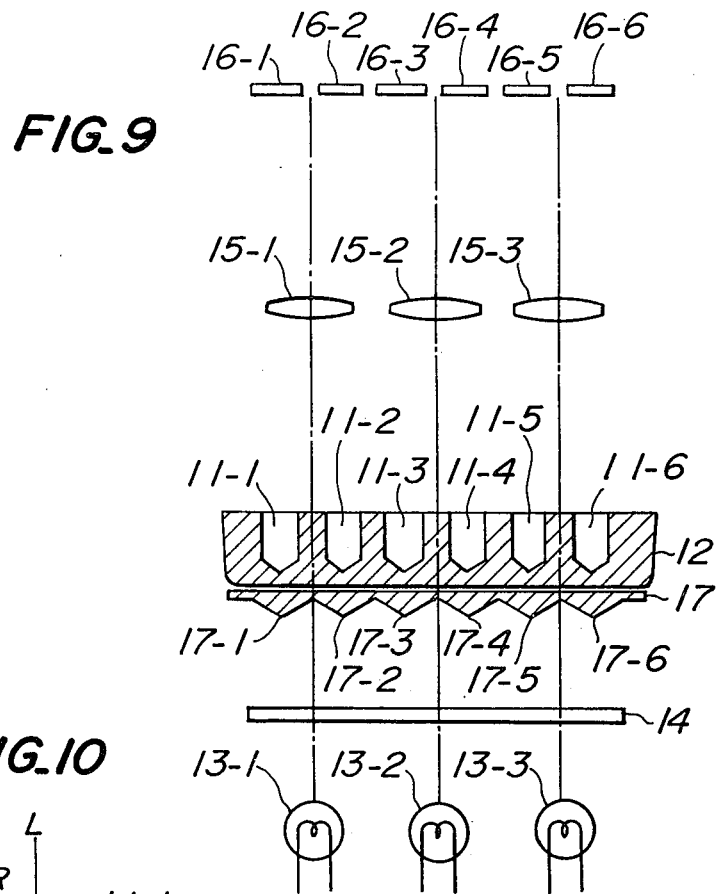
FIG. 9 is a schematic view illustrating another embodiment of the detecting apparatus according to the invention.
Figure 10:
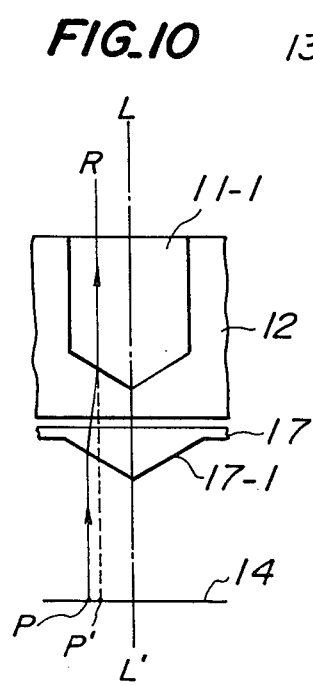
FIG. 10 is a schematic view for explaining how to obtain a uniform brightness image of a bottom surface in the apparatus of FIG. 9.

FIG. 9 is a schematic view illustrating another embodiment of the detecting apparatus according to the invention. In this embodiment, light sources 13-1 to 13-3 and a diffusion plate 14 are arranged underneath an optical correction plate 17 which is arranged immediately below a microplate 12 having reaction vessels 11-1 to 11-6 and objective lens 15-1 to 15-3 and light detectors 16-1 to 16-6 are arranged above the microplate 12. In such an arrangement, as shown in FIG. 10 a light ray emanating from an arbitrary point P on the diffusion plate 14 is refracted by a conical projection 17-1 and a bottom surface of the reaction vessel 11-1 in a direction R. Therefore, this light ray is seemed to emanate from a point P' which is very close to the original point P and thus, the image of the bottom surface becomes much more uniform as compared with the known apparatus shown in FIG. 5. Therefore, also in this embodiment, it is possible to detect the particle agglutination pattern with a high precision.

Figure 11:
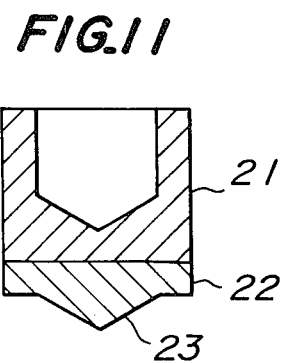
FIG. 11 is a cross sectional view depicting another embodiment of the detecting apparatus according to the invention.

The present invention is not limited to the embodiments explained above, but may be modified in various manners. In the above embodiments, the optical correction plate is fixedly arranged below the reaction vessel, but in an embodiment illustrated in FIG. 11 an optical correction plate 22 having a conical projection 23 is secured to a rear surface of a reaction vessel 21. Similarly an optical correction plate having a number of conical projections formed therein in a matrix form may be secured onto a rear surface of a microplate in which a number of reaction vessels are formed in a matrix form. Further the reaction vessel and the optical correction plate may be integrally formed by, for instance, molding.

As described above in detail, according to the invention since the optical correction plate having the projection a contour of which is substantially identical with that of the bottom surface of the reaction vessel is provided underneath the reaction vessel, an image of the bottom surface of the reaction vessel having substantially uniform brightness can be formed on the light detector. Therefore, the electrical signal having a high signal to noise ratio can be derived and thus, the particle agglutination pattern formed on the bottom surface can be detected very precisely and accurately.

What is claimed is:

1. An apparatus for detecting photoelectrically a particle agglutination pattern formed on a bottom surface of a reaction vessel, at least a part of the bottom surface being inclined with respect to the horizontal plane, comprising
    means for illuminating the particle agglutination pattern formed on the bottom surface of the reaction vessel;
    means for forming an image of the particle agglutination pattern formed on the bottom surface;
    means for converting the image of the particle agglutination pattern into an electrical signal representing the particle agglutination pattern; and
    means arranged underneath the reaction vessel and having a projection a contour of which is substantially identical with that of the bottom surface to correct a non-uniformity in brightness of an image of the bottom surface formed on the converting means.

2. An apparatus according to claim 1, wherein said illuminating means comprises a light source and a diffusion plate arranged between the light source and the reaction vessel.

3. An apparatus according to claim 1, wherein said image forming means comprises an objective lens having a long focal depth.

4. An apparatus according to claim 1, wherein said converting means comprises a light detector having a circular light receiving region and a ring-shaped light receiving region arranged coaxially with said circular light receiving region, and a differential amplifier for deriving a difference between output signals supplied from the circular and ring-shaped light receiving regions.

5. An apparatus according to claim 1, wherein said correcting means comprises a transparent plate having the projection in that surface which is remote from the reaction vessel.

6. An apparatus according to claim 5, wherein said projection is made conical.

7. An apparatus according to claim 5, wherein said plate is placed immediately below the reaction vessel.

8. An apparatus according to claim 5, wherein said plate is secured to a rear surface of the reaction vessel.

9. An apparatus according to claim 5, wherein said plate is made of the same material as that of the reaction vessel.

10. An apparatus according to claim 5, wherein said plate has a plurality of projections corresponding to a plurality of reaction vessels formed in a microplate in a matrix form.

11. An apparatus according to claim 10, wherein said plurality of projections are aligned in a row corresponding to a row of the reaction vessels in the microplate.

12. An apparatus according to claim 11, wherein each of said plurality of projections is formed in a conical shape.

13. An apparatus according to claim 12, wherein said plate is arranged immediately below the microplate in such a manner that apexes of the conical projections are made aligned with the lowermost central portions of the conical bottom surfaces of the reaction vessels in the row.

14. An apparatus according to claim 12, wherein said plate is secured to a rear surface of the microplate in such a manner that apexes of the conical projections are made aligned with the lowermost central portions of the conical bottom surfaces of the reaction vessels in the row.

15. An apparatus according to claim 1, wherein said projection is integrally formed with the reaction vessel on its rear surface.

16. An apparatus according to any one of claims 1 to 15, wherein said illuminating means is arranged above the reaction vessel and said image forming means and converting means are arranged below the reaction vessel.

17. An apparatus according to any one of claims 1 to 15, wherein said illuminating means is arranged below the reaction vessel and said image forming means and converting means are arranged above the reaction vessel.

18. An apparatus for detecting photoelectrically an agglutination pattern formed within a reaction vessel having a longitudinal central axis and having a transparent bottom comprising a substantially conical first surface, said first conical surface having a peripheral portion and a central portion, said apparatus comprising:
    means for illuminating the bottom of the reaction vessel so as to enable a determination of whether an agglutination pattern has formed;
    optical correction means for transmitting light rays which have been transmitted through the bottom of the reaction vessel, said optical correction means having a substantially conical second surface and being positioned such that the apex of said first conical surface is aligned on the central axis with the apex of the second conical surface;
    means for detecting light rays which have illuminated said first conical surface and have been refracted by said correction means;

whereby said correction means operates to refract the light rays transmitted through the bottom of the reaction vessel such that when the reaction vessel is empty said detecting means is evenly illuminated and when the reaction vessel is filled the detection of the particle agglutination pattern by said detecting means may be accomplished with a high degree of precision.

19. The apparatus of claim 18 wherein said detecting means comprises first and second portions arranged so that light rays illuminating the peripheral and central portions of said first conical surface illuminate said first and second portions respectively in substantially mutually exclusive fashion, said detecting means further comprising comparison means for comparing the illumination of said first and second portions such that when an agglutination reaction proceeds in the reaction vessel and agglutinated particles are uniformly distributed on said first surface said comparison means produces a first signal and when no agglutination reaction occurs and descending particles are centrally collected, said comparison means produces a second signal.

20. The apparatus of claim 18 or 19 wherein the bottom of the reaction vessel further comprises a substantially flat first external surface and said correction means comprises a substantially flat second external surface, said first and second external surfaces being arranged substantially parallel to each other and perpendicular to said central axis.

21. The apparatus of claim 20 wherein said first and second external surfaces are spaced from one another.

22. The apparatus of claim 18 or 19 wherein the surface of the bottom of the reaction vessel opposite the first conical surface is substantially flat and the surface of the optical correction means opposite said second conical surface is substantially flat and contiguous with said substantially flat surface of the bottom of the reaction vessel.

23. The apparatus of claim 18 or 19 wherein said optical correction means is integrally formed on the reaction vessel.

24. The apparatus of claim 18 or 19 wherein the contour of said first conical surface is substantially identical to the contour of the second conical surface.

* * * * *